United States Patent
Pogue et al.

(10) Patent No.: US 6,377,842 B1
(45) Date of Patent: Apr. 23, 2002

(54) METHOD FOR QUANTITATIVE MEASUREMENT OF FLUORESCENT AND PHOSPHORESCENT DRUGS WITHIN TISSUE UTILIZING A FIBER OPTIC PROBE

(75) Inventors: Brian William Pogue, Wilder, VT (US); Gregory Charles Burke, Hanover, NH (US)

(73) Assignee: Aurora Optics, Inc., West Lebanon, NH (US)

( * ) Notice: Subject to any disclaimer, the term of this patent is extended or adjusted under 35 U.S.C. 154(b) by 0 days.

(21) Appl. No.: 09/379,001

(22) Filed: Aug. 23, 1999

Related U.S. Application Data

(60) Provisional application No. 60/101,407, filed on Sep. 22, 1998.

(51) Int. Cl.$^7$ .................................................. A61B 5/00
(52) U.S. Cl. .................... 600/478; 600/476; 250/458.1; 250/459.1; 356/317; 436/172
(58) Field of Search ................................. 600/476, 478, 600/473, 310, 312, 329, 342; 250/458.1, 459.1; 356/317; 436/172

(56) References Cited

U.S. PATENT DOCUMENTS

| | | |
|---|---|---|
| 4,785,806 A | 11/1988 | Deckelbaum |
| 4,957,114 A | 9/1990 | Zeng et al. |
| 5,009,655 A | 4/1991 | Daignault et al. |
| 5,062,431 A | 11/1991 | Potter |

(List continued on next page.)

FOREIGN PATENT DOCUMENTS

| | | | |
|---|---|---|---|
| EP | 0 594 388 | * | 8/1992 |
| EP | 0 832 598 A2 | * | 10/1997 |
| EP | 832598 A2 | | 4/1998 |

(List continued on next page.)

OTHER PUBLICATIONS

M. Kriegmair, R. Baumgartner, R. Knuchel, H. Stepp, F. Hofstadter, and A. Hofstetter, "Detection of Early Bladder Cancer by 5–Aminolevulinic Acid Induced Porphyrin Fluorescence", J. Urol. 155, 105–110 (1996).

S. Andersson–Engels, J. Ankerst, J. Johansson, K. Svanberg, and S. Svanberg, "Laser–Induced Fluorescence in Malignant and Normal Tissue of Rats Injected with BPD", Photochem. Photobiol. 57, 978–83 (1993).

K. T. Schomacker, J. K. Frisoli, C. C. Compton, T. J. Flotte, J. M. Richter, N. S. Nishioka, and T. F. Deutsch, "Ultraviolet Laser–Induced Fluorescence of Colonic Tissue: Basic Biology and Diagnostic Potential", Lasers Surg. Med. 12, 63–78 (1992).

(List continued on next page.)

*Primary Examiner*—Marvin M. Lateef
*Assistant Examiner*—Talaya James

(57) ABSTRACT

A fiber optic based probe has been designed to sample the fluorescence or phosphorescence signal from animal or human tissues, such that the light intensity is not multiply scattered. This type of measurement allows a linear detection of the concentration of the luminescent compound non-invasively from the tissue. The basic principle of the fiber probe is to use fiber optics which are smaller in diameter that the average scattering length of the tissue. In order to increase the detected signal to a stronger level, multiple fibers are used by spacing them out on the surface of the tissue so that each fiber samples an isolated section of tissue. Each fiber delivers the excitation light to the tissue, and receives the emission light from the tissue. All fibers are coupled into the same detector to integrate the overall signal. Sampling of the scattered excitation signal intensity is also done to correct for changes in the scattering coefficient between tissues. This fiber bundle can be used to quantify the concentration of fluorescence or phosphorescent chemicals in vivo non-invasively. One application of this device is as a dosimetry tool, to monitor photosensitizer drug concentration within tissue for photodynamic therapy.

13 Claims, 7 Drawing Sheets

U.S. PATENT DOCUMENTS

| | | | |
|---|---|---|---|
| 5,106,387 A | | 4/1992 | Kittrell et al. |
| 5,111,641 A | | 5/1992 | Brown et al. |
| 5,205,291 A | | 4/1993 | Potter |
| 5,293,872 A | | 3/1994 | Alfano et al. |
| 5,318,023 A | | 6/1994 | Vari et al. |
| 5,335,305 A | * | 8/1994 | Kose et al. ............... 385/147 |
| 5,350,375 A | | 9/1994 | Deckelbaum et al. |
| 5,368,841 A | | 11/1994 | Trauner et al. |
| 5,377,676 A | | 1/1995 | Vari et al. |
| 5,419,323 A | | 5/1995 | Kittrell et al. |
| 5,421,337 A | | 6/1995 | Richards-Kortem et al. |
| 5,450,857 A | | 9/1995 | Garfield et al. |
| 5,452,723 A | | 9/1995 | Wu et al. |
| 5,467,767 A | | 11/1995 | Alfano et al. |
| 5,483,958 A | | 1/1996 | Merberg et al. |
| 5,498,324 A | * | 3/1996 | Yeung et al. ............... 204/452 |
| 5,503,559 A | | 4/1996 | Vari et al. |
| 5,533,508 A | | 7/1996 | Dioron |
| 5,562,100 A | | 10/1996 | Kittrell et al. |
| 5,572,996 A | | 11/1996 | Doiron |
| 5,590,660 A | | 1/1997 | MacAulay et al. |
| 5,591,981 A | | 1/1997 | Heffelfinger et al. |
| 5,612,540 A | | 3/1997 | Richards-Kortem et al. |
| 5,628,310 A | | 5/1997 | Rao et al. |
| 5,639,668 A | * | 6/1997 | Neel et al. ............... 436/172 |
| 5,678,550 A | | 10/1997 | Bassen et al. |
| 5,697,373 A | | 12/1997 | Richards-Kortem et al. |
| 5,699,795 A | | 12/1997 | Richards-Kortem et al. |
| 5,701,902 A | * | 12/1997 | Vari et al. ............... 600/473 |
| 5,713,364 A | | 2/1998 | DeBaryshe et al. |
| 6,008,055 A | * | 6/1998 | Zhu et al. ............... 436/172 |
| 5,784,152 A | | 7/1998 | Heffelfinger et al. |
| 5,823,993 A | | 10/1998 | Lemelson |
| 5,827,190 A | | 10/1998 | Palcic et al. |

FOREIGN PATENT DOCUMENTS

| | | |
|---|---|---|
| EP | 834277 A1 | 4/1998 |
| EP | 860142 A2 | 8/1998 |
| EP | 872211 A1 | 10/1998 |
| WO | 97/19632 | 6/1997 |
| WO | 97/47233 | 12/1997 |
| WO | 98/00057 | 1/1998 |
| WO | 98/04187 | 2/1998 |
| WO | 98/24360 | 6/1998 |
| WO | 98/32370 | 7/1998 |
| WO | 98/34533 | 8/1998 |
| WO | 98/41140 | 9/1998 |
| WO | 98/43096 | 10/1998 |
| WO | 98/44841 | 10/1998 |
| WO | 98/44842 | 10/1998 |
| WO | 98/46123 | 10/1998 |
| WO | 98/51209 | 11/1998 |
| WO | 98/52460 | 11/1998 |
| WO | 98/53733 | 12/1998 |
| WO | 98/57577 | 12/1998 |

OTHER PUBLICATIONS

R. Richards–Kortum, M. R. Mitchell, N. Ramanujam, A. Mahadevan, and S. Thomsen, "In vivo fluorescence spectroscopy: potential for non–invasive, automated diagnosis of cervical intraepithelial neoplasia and use as a surrogate endpoint biomarker", J. Cell. Biochem. (Suppl.) 19, 111–119 (1994).

S. L. Jacques, R. Joseph, and G. Gofstein, "How photobleaching affects dosimetry and fluorescence monitoring of PDT in turbid media", in *Optical Methods for Tumor Treatment and Detection: Mechanisms and Techniques in Photodynamic Therapy II,* ed. (T. J. Dougherty), Proc. SPIE 1881, 168–179 (1993).

M. Sinaasappel and H. J. C. M. Sterenborg, "Quantification of the hematoporphyrin derivative by fluorescence measurement using dual–wavelength excitation and dual–wavelength detection", Appl. Opt. 32, 541–8 (1993).

D. Braichotte, J. F. Savary, P. Monnier, H. van den Bergh, "Enhanced Photodynamic Therapy and Dosimetry by Light Induced Fluorescence", in *5th International Photodynamic Association Biennial Meeting,* ed. (D. A. Cortese), Proceeding of SPIE 2371, 120–124 (1995).

J. K. Frisoli, E. G. Tudor, T. J. Flotte, T. Hasan, T. F. Deutsch, and K. T. Schomacker, "Pharmacokinetics of a Fluorescent Drug Using Laser–Induced Fluorescence", Cancer Res. 53, 5954–61 (1993).

G. R. Martin and R. K. Jain, "Noninvasive Measurement of Interstital pH Profiles in Normal and Neoplastic Tissue Using Fluorescence Ratio Imaging Microscopy", Cancer Res. 54, 5670–4 (1994).

M. Bellmunt, M. Portero, R. Pamplona, M. Muntaner, and J. Prat, "Age–Related Fluorescence in Rat Lung Collagen", Lung 173, 177–185 (1995).

M. Panjehpour, R. E. Sneed, D. L. Frazier, M. A. Barnhill, S. F. O'Brien, W. Harb, and B. F. Overholt, "Quantification of Phthalocyanine Concentration in Rat Tissue Using Laser–Induced Fluorescence Spectroscopy", Lasers Surg. Med. 13, 23–30 (1993).

S. Lam, J. Hung, and B. Palcic, "Mechanism of Detection of Early Lung Cancer by Ratio Fluorometry", Lasers Life Sci. 4 (1991).

J. Wu, M. S. Feld, and R. P. Rava, "Analytical model for extracting intrinsic fluorescence in turbid media", Appl. Opt. 32, 3585–95 (1993).

M. S. Patterson and B. W. Pogue, "Mathematical model for time–resolved and frequency–domain fluorescence spectroscopy in biological tissues", Appl. Opt. 33, 1963–74 (1994).

A. J. Durkin, S. Jaikumar, N. Ramanujam, and R. Richards–Kortum, "Relation between fluorescence spectra of dilute and turbid samples", Appl. Opt. 33, 414–423 (1994).

C. L. Hutchinson, J. R. Lakowicz, and E. M. Sevick–Muraca, "Fluorescence Lifetime–Based Sensing in Tissues: A Computational Study", Biophys. J. 68, 1574–82, (1995).

D. Y. Paithankar, A. U. Chen, B. W. Pogue, M. S. Patterson, and E. M. Sevick–Muraca, "Imaging of fluorescent yield and lifetime from multiply scattered light re–emitted from tissues and other random media", Appl. Opt. 36, 2260–72 (1997).

J. Chang, H. L. Graber, R. L. Barbour, "Luminescence optical tomography of dense scattering media", J. Opt. Soc. Am. A 14, 288–299 (1997).

S. Zeng, C. MacAulay, D. I. McLean, and B. Palcic, "Spectroscopic and Microscopic Characteristics of Human Skin Autofluorescence Emission", Photochem Photobiol 61, 639–645 (1995).

H. S. Zeng, C. MacAulay, D. I. McLean, "Reconstruction of in vivo skin autofluorescence spectrum from microscopic properties by Monte Carlo simulation", J. Photochem Photobiol B 38, 234–240 (1997).

R. J. Crilly, W. F. Cheong, B. C. Wilson, and J. R. Spears, "Forward–adjoint fluorescence model: Monte Carlo integration and experimental validation," Appl. Opt. 36 (25) 6513–6519 (1997).

A. J. Welch, C. Gardner, R. Richards–Kortum, E. Chan, G. Criswell, J. Pfefer, and S. Warren, "Propagation of Fluorescent Light," Lasers Surg. Med. 21, 166–178 (1997).

B. W. Pogue and T. Hasan, "Fluorophore Quantitation in Tissue–Simulating Media with Confocal Detection," IEEE J. Quan. Electr. 2, 959–964 (1997).

B. W. Pogue and T. Hasan, "Quantitative fluorescence measurements from tissue using confocal detection," in *Laser–Tissue Interaction VIII*, ed. (S. L. Jacques), Proceedings of SPIE 2975, 202–207 (1997).

L. Wang and S. Jacques, "Monte Carlo Modeling of Light Transport in Multi–Layered Tissues in Standard C." University of Texas, M. D. Anderson Cancer Center, Houston (1992–1993).

Testorf M., Osterberg U. L., Pogue, B. W., Paulsen, K. D. "Sampling of time and frequency domain signals in Monte Carlo simulations of photon migration", (submitted to Applied Optics, 1998).

J. R. Mourant, J. Boyer, A. H. Hielscher, I. J. Bigio, "Influence of the scattering phase function on light transport measurements in turbid media performed with small source–detector separations", Opt. Lett. 21, 546–548 (1996).

W.–F. Cheong, "Summary of optical properties", in *Optical Thermal Response of Laser–Irradiated Tissue.* Ed. A. J. Welch, and M. J. C. van Gemert, (Plenum Press: New York, 1995) pp. 275–303.

H. J. van Staveren, C. J. M. Moes, J. van Marle, S. A. Prahl, and M. J. C.. van Gemert, Light Scattering in Intralipid–10% in the wavelength range of 400–1100nm, Appl. Opt. 30, 4507–14 (1991).

S. J. Madsen, M. S. Patterson, and B. C. Wilson, "The use of India ink as an optical absorber in tissue–simulating phantoms", Phys. Med. Biol. 37, 985–993 (1992).

Cheong, W.–F., Prahl, S. A., Welch, A. J., "A Review of the Optical Properties of Biological Tissues", IEEE J. Quan. Electr. 26, 2166–2185 (1990).

Wu, J., Partovi, F., Feld, M. S., Rava, R. P., "Diffuse Reflectance from Turbid Media: An Analytical Model of Photon Migration".

Ramanujam, N., Mitchell, M. F., Mahadevan, A., Thomsen, S., Silva, E., Richards–Kortum, R., "Fluorescence Spectroscopy: A Diagnostic Tool for Cervical Intraepithelial Neoplasia (CIN)", Gynecologic Oncology 52, 31–38 (1994).

Hutchinson, C., Troy, T. L., Sevick–Muraca, E. M., "Fluorescence–lifetime determination in tissues or other scattering media from measurement of excitation and emission kinetics", Applied Optics 35, 2325–2332 (1996).

Brennan, J. F., Zonios, G. I., Wang, T. D., Rava, R. P., Hayes, G. B., Dasari, R. R., Feld, M. S., "Portable Laser Spectrofluorimeter System for in Vivo Human Tissue Fluorescence Studies", Applied Spectroscopy 47, 2081–2086 (1993).

Lam, S., MacAulay, C., Hung, J., LeRiche, J., Profio, A. E., Palcic, B., "Detection of dysplasia and carcinoma in situ with a lung imaging fluorescence endoscope device", J. Thoracic & Cardiovascular Surg, 1035–1040 (1993).

* cited by examiner

METHOD FOR QUANTITATIVE MEASUREMENT OF FLUORESCENT AND PHOSPHORESCENT DRUGS WITHIN TISSUE UTILIZING A FIBER OPTIC PROBE

This application claims benefit to provisional application No. 60/101,407 filed Sep. 22, 1998.

BACKGROUND OF INVENTION

This invention consists of an improved method for the use of fiber optics as a means to evaluate human and animal bodily tissues.

Fluorescence detection from tissue is increasingly being used as a diagnostic probe to either detect early cancer, to monitor treatment dose in photodynamic therapy, to monitor fluorescent drug pharmacokinetics, or to assay for fluorescent reporters of metabolic processes. It is well recognized that the pigments of a tissue may reduce the intensity of a light signal, so that fluorescence measurements from one sample cannot be directly compared to another without some type of empirical calibration. Also variation in blood flow and tissue heterogeneity can confound a series of fluorescence measurements, due to the fact that the excitation and fluorescent light are multiply scattered. At present there is no standard method for quantitative tissue fluorescence measurement in vivo, and many investigators rely upon the use of radioactive labeling or tissue extraction methods to yield quantitative drug uptake measurements. A new type of fiber optic probe has been developed and tested here in tissue-simulating phantoms, which is insensitive to the local background absorbing molecules, and detects fluorescence signals which are linearly proportional to the fluorophore concentration. This design allows quantitative measurement of fluorophore concentration for certain applications, and minimizes the need for expensive and time consuming tissue extraction or radio-labeling methods. This fiber optic method may allow non-invasive quantification of fluorescence for any applications where the inter-sample variations of tissue optical properties affect the measurements.

The prior art teaches that most tissue fluorescence measurements use large core fiber bundles, or separate source-detector fibers which allow the excitation and emission light to be multiply scattered in the tissue, and hence the fluorescence intensity is affected by the long pathlength of travel in the tissue. One practical approach to quantitative tissue fluorescence measurements has been to use relative fluorescence as a ratio at two different wavelengths, or from comparing the fluorescence intensity of two different species present in the tissue. These approaches suffer from problems in calibration and wavelength variations in the tissue optical properties; hence, the measurements must be carefully interpreted. Alternatively, several researchers have developed models of fluorescence propagation in tissue to predict fluorescence signals from multiple scattering samples such as tissue for a given fluorophore concentration. By applying time-resolved or frequency-domain instrumentation, the lifetimes and concentrations of a fluorophore can be calculated, assuming that the light propagation in the tissue can be accurately modeled by diffusion theory, or with Monte Carlo scattering models. The diffusion theory approach has the constraint that the region of tissue sampled needs to be sufficiently large and homogenous. The Monte Carlo approach is generally used to exactly model the tissue geometry with boundaries and changes in optical properties at the microscopic level. This latter approach can be very successful, but is limited to applications where the tissue properties and layers are well understood. Both of these methods require some apriori knowledge about the tissue in order to quantitatively estimate the fluorophore concentration from the detected signal.

Alternatively fluorescence measurements can be obtained from tissue using very small sample volumes, and by confining the region of tissue probed to a diameter smaller than the average scattering length, where the effects of tissue scatter and absorption can be minimized. This latter approach has the benefit of significantly minimizing the tissue effects upon the detected fluorescence signal so that intensity variations due to the tissue intrinsic chromophores are not detected. Practical implementation of this approach requires limiting the detected volume of tissue to a region smaller than the typical mean free path for scattering in tissue, which is approximately 100 microns (a micron is equal to one millionth of a meter). While limiting the volume of tissue sampled can significantly lower the detected fluorescence signal, current light detectors can be used to quantify fluorescence from sub-micromolar levels of some photosensitizers. This concept was demonstrated using confocal detection both in tissue phantoms and excised tissues. This study extends that work to examine the use of small fiber optics to measure minimally scattered fluorescence from tissue-simulating media in this manner. To realize this experimentally, a new fiber optic bundle is demonstrated which allows detection of fluorescence from confined regions of tissue, while sampling from multiple locations simultaneously to maximize the detected signal. Applications of this system will likely be in non-invasively measuring luminescent drugs taken up in vivo, and monitoring pharmacokinetics of fluorescently labeled metabolites non-invasively.

SUMMARY OF INVENTION

A new design for a fiber optic bundle was demonstrated to measure fluorescence signals from tissue, where the intensity of the signal is not significantly affected by the medium's absorption and scattering coefficients, and hence only depends upon the fluorophore's properties. Monte Carlo simulations of light scattering were used to design and verify the results obtained. The fiber optic bundle was tested on tissue-simulating phantoms and compared to the use of a standard non-imaging fiber optic bundle. The new bundle was composed of 30 individual 100 $\mu$m ("$\mu$m" is used as the abbreviation for diameter in microns) fibers, where each fiber was separated by approximately 1 mm ("mm" is used as the abbreviation for millimeters) from each other fiber on the end of the bundle which contacts the tissue surface and are without separation on the opposite end. This design allows integration of the signal over several locations, while maintaining localized sampling from regions smaller than the average mean free scattering path of the tissue. The bundle was tested by measuring fluorescence signals from tissue-simulating solutions containing a fluorescent compound. These studies demonstrate that the new bundle reduces the effect of the intrinsic absorption in the medium, allowing detection of fluorescence that is linearly proportional to the fluorophore concentration.

DESCRIPTION OF THE PREFERRED EMBODIMENTS

The invention includes a fiber probe that is used with fiber optics smaller in diameter that the average scattering length of the tissue. The detected signal is increased through the placement of multiple fibers on the surface of the tissue so that each fiber samples an isolated section of tissue. Each fiber delivers the excitation light to the tissue, and receives the emission light from the tissue. All fibers are coupled into the same detector to integrate the overall signal. Adjustments to excitation signal intensity are performed to correct for changes in the scattering coefficient between tissues.

Experiments

The goal of the experimental work was to develop a small fiber optic system which could be used to deliver excitation light to a tissue sample and to detect the emission from the same fiber using fiber optics of 100 $\mu$m or less. Preliminary attempts to develop such a system were limited by the minimal light which was captured by the fiber resulting in a very noisy signal. As a more practical approach, a novel multi-strand fiber bundle was developed to increase the light detected signal while maintaining isolated sampling of fluorescence from the tissue (schematic shown in FIG. 4). Monte Carlo simulations shown in the Results section, indicated that if each fiber was separated by more than a 500 $\mu$m radius center-to-center from the other fibers, there would be less than 10% interaction (or crosstalk through the tissue) between the signals from the fibers. The exact level of crosstalk would depend on the optical properties of the tissue, in that more highly scattering or highly pigmented tissues would attenuate the light more and decrease the inter-fiber crosstalk through the tissue, and vice versa.

Figure 4:
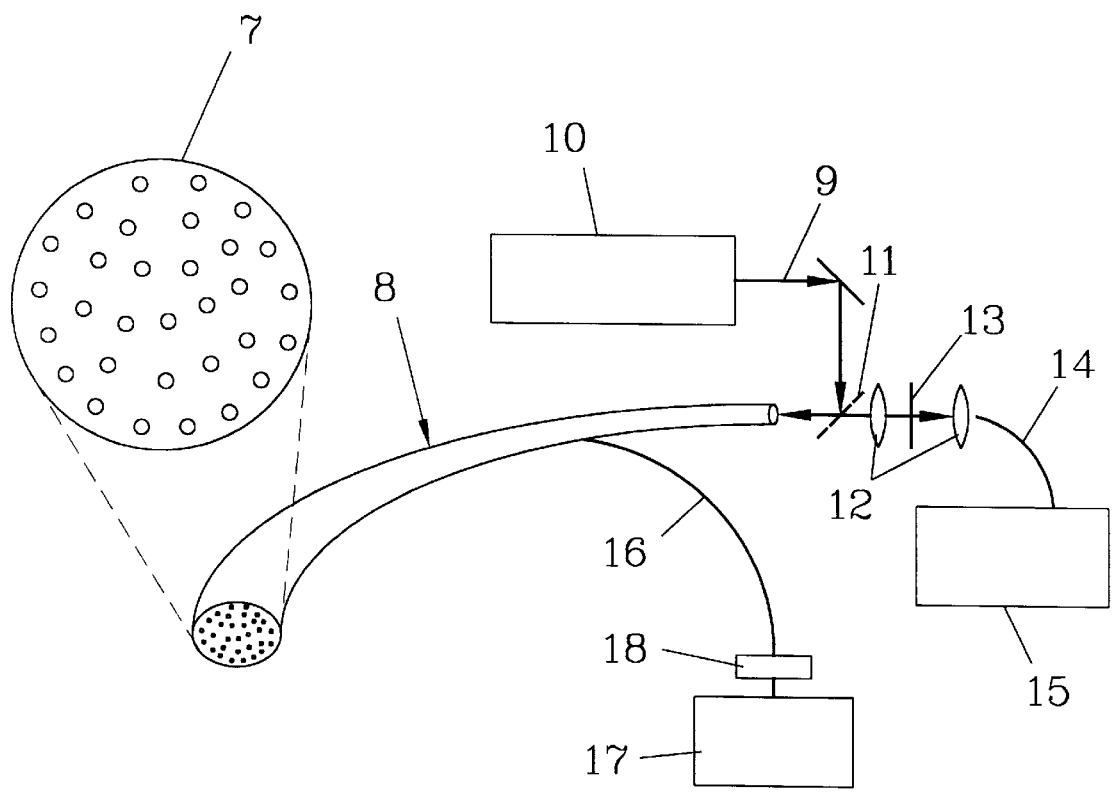
FIG. 4. Schematic diagram of the apparatus, including an enlarged view of the end of the fiber optic probe 7 designed for these measurements. The fiber optic bundle 8 consisted of 30 individual fibers, each 100 $\mu$m core diameter, with the interfiber separation increased to 1 mm average on the tissue contact end, and without any separation on the opposite end. Excitation light 9 from an Argon laser 10 was delivered to the fiber bundle by reflection from a dichroic mirror 11. The captured fluorescent light was transmitted through the dichroic, and collected by a lens system 12, through a rejection filter 13, and into a fiber coupled 14 photomultiplier tube 15. The current from the photomultiplier tubes was measured with an oscilloscope terminated in 50 Ohms, and the intensity in mV ("mV" being the abbreviation for "milli-volts") for each measurement is plotted in FIGS. 5(b) and 6. A single fiber 16 was used from the bundle to sample the excitation light intensity reflected from the tissue surface, by filtering out the emission light 18 and detecting the intensity with a second photomultiplier tube 17. The system was tested on tissue-simulating solutions with a fluorophore added to it.

The prototype multi-strand fiber was constructed with 100 $\mu$m fiber optics, using an inter-fiber spacing between 0.5 mm to 1 mm on the tissue contact surface (see FIG. 4). A total of 30 fibers were included in this bundle, and light was coupled into and out of the fiber with a standard fluorescence microscope arrangement of a dichroic mirror and rejection filter. The excitation beam was directed onto the end of the multi-strand fiber bundle, with approximately 1 mm diameter. The emission light was captured from the end of the fiber bundle after passing through the dichroic mirror and onto a focusing lens. A rejection filter removed the scattered excitation light, before the beam was then focused into another fiber which lead to the photomultiplier tube detector. A multi-line argon laser, running at approximately 20 mW, was used as the excitation source, and the fluorescent compound used was sulphorhodamine B (Exciton Inc., N.J.) dissolved in a stock solution of 5 mM in ethylene glycol. This fluorescent dye was chosen simply to illustrate the potential of the system with a standard small Argon laser for excitation, while more physiologically relevant dyes can be used with another laser source for excitation. The dye has a high extinction at 488 and 514 nm, the excitation maximum of the laser, and has a peak fluorescence emission at 635 nm with fluorescent quantum yield of $\phi_{fl}$=0.7. The tissue simulating samples were mixed with 1% Intralipid by volume, which is a well known tissue-simulating medium, with scattering coefficients of 7.9 mm$^{-1}$ and 4.7 mm$^{-1}$, at 514 nm and 635 nm respectively. In order to simulate the absorbing pigment present in tissue, such as melanin or hemoglobin, an inert absorber was needed, and India ink was used for this case since it has a relatively constant absorbance across the visible spectrum. Preliminary measurements were taken to assess the absorption coefficient of the ink, and it was found to be 5.0 mm$^{-1}$ for a 1% stock solution by volume, at 633 nm. The wavelength variation over the region 514 to 635 nm is less than 5%. Two series of solutions were prepared with serial dilutions of the fluorophore, one with no ink present ($\mu_a$=0.0026 mm$^{-1}$) and one with 0.1 ml of the ink stock solution added to each 7 ml sample ($\mu_1$=0.073 mm$^{-1}$). While the absorption coefficient of different tissues varies considerably, this range of coefficients agrees well with skin, brain, and fat over most wavelength ranges and muscle and liver, in the red region of the spectrum. A more detailed study is needed for application in darker tissues such as liver and muscle in the blue-green region of the spectrum.

Each tissue-simulating sample was measured for fluorescence with the new fiber bundle, and with a standard 1 mm fiber bundle (Edmond Scientific, Barrington N.J.) for comparison. The standard fiber bundle was a multi-strand quartz fiber bundle of 50 micron fibers with no coherence preservation, with a total outer diameter of 1 mm.

Monte Carlo simulations of the fluence in the medium are shown for three different fiber diameters, in FIG. 2. In the upper three panels, the excitation fluence is reported for an infinite incident diameter (left), a 2 mm incident diameter (middle), and a 100 micron incident diameter fiber (right). The lower three panels depict the fluorescent fluence which is eventually captured by the fiber for the same three fiber diameters, respectively. This latter fluence was calculated by selecting only those photon paths which end up passing into the fiber after scattering in the medium. These simulations required 10$^7$ photon packets, which took 30 minutes of computation time for each image on a 233 MHz Pentium processor.

Simulations were completed for a series of fiber diameters between 100 mm and 20 $\mu$m where the average number of elastic scattering events in both the excitation signal and the fluorescence signal were calculated. The results are plotted in FIG. 3. Optical properties of the medium were the same as in FIG. 2. Photon packets which re-entered the fiber were counted in the simulation, and binned as either excitation or fluorescent photons. The number of elastic scatter events that each photon packet underwent before detection was recorded, and multiple packets were averaged to obtain statistics on the number of elastic scattering events in the signal. This was repeated for each particular fiber radius simulated.

Simulations were used to calculate the intensity signal detected from a fiber optic using the same medium optical properties as above for a series of fluorophore concentrations using both a 1 mm fiber optic and a 100 $\mu$m fiber optic. These calculations are plotted in FIG. 5($a$), as a theoretical comparison to the experimental measurements. Two different endogenous absorption values were used for each fiber size, first with $\mu_a$=0.003 mm$^{-1}$ and with $\mu_a$=0.030 mm$^{-1}$ (corresponding to low and high absorption in the FIG. 5($a$)).

Measurements using the fiber optic system shown in FIG. 4 were taken with solutions of 1% Intralipid, with increasing amounts of sulphorhodamine dye. The fluorescence versus dye concentration was measured for two different concentrations of India ink in solution (to simulate endogenous absorber). The fluorescence measurements were repeated for a standard 1 mm diameter fiber bundle for comparison. All of these measurements are plotted in FIG. 5($b$). The data of fluorescence versus fluorophore concentration is linear when the slope on the log-log graph equals 1.0, and the slopes for the standard fiber optic bundle used here are 0.82 and 0.89, corresponding to high and low absorption coefficient respectively (FIG. 5). The slopes of log fluorescence versus log fluorophore concentration are 0.98 and 1.00 when the new fiber optic bundle is used, for low and high absorption respectively (FIG. 5).

Figure 6:
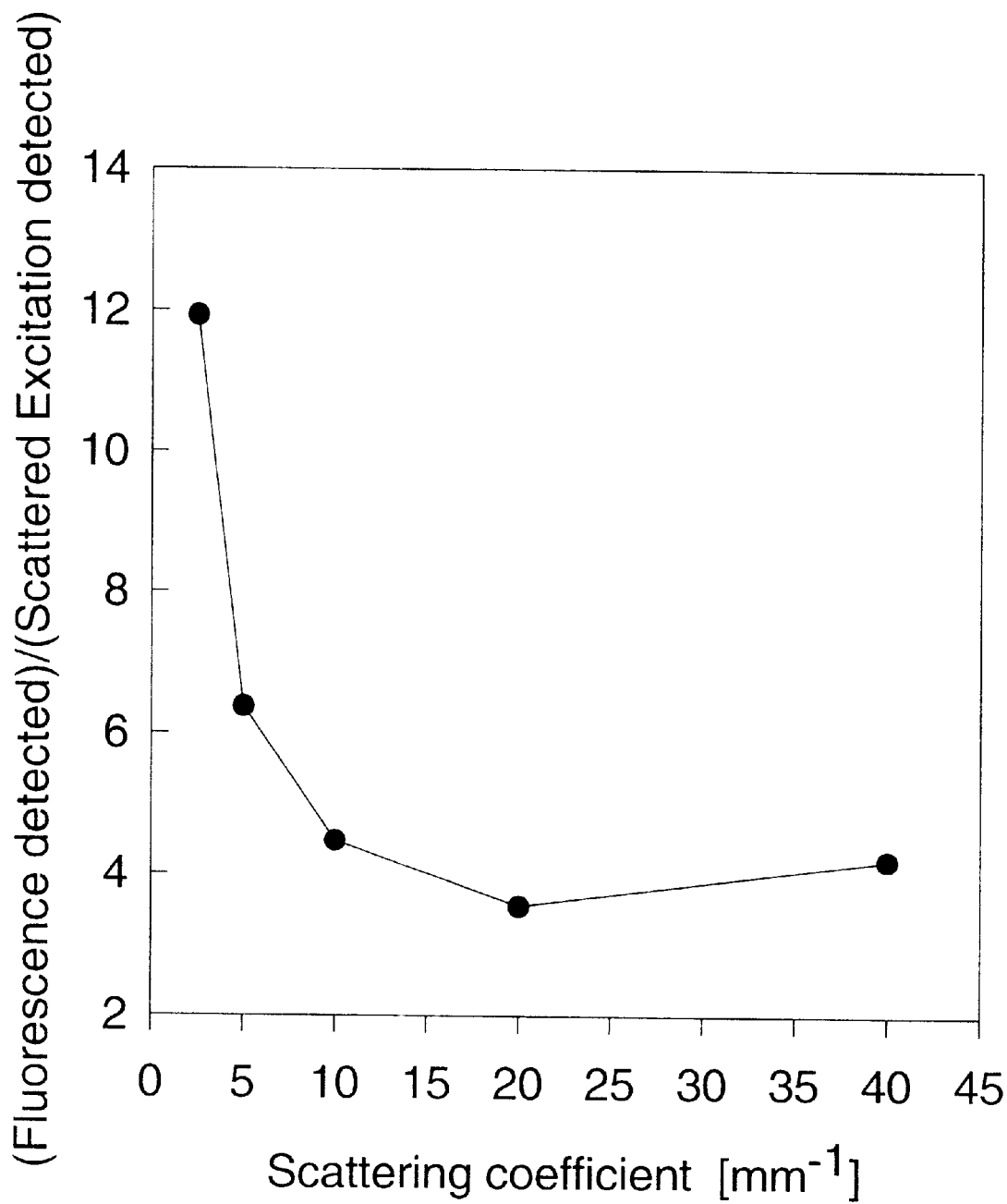
FIG. 6. Fluorescence (at 650 nm) ("nm" is the abbreviation for "nanometer" which is equal to one billionth of a meter) and scattered excitation light (at 488 and 514 nm) were detected from several solutions, all containing a constant 62 $\mu$M of fluorophore, but with increasing concentration of Intralipid, and hence increasing scattering coefficient. Here the ratio is plotted of fluorescence/scattered light. The background absorption coefficient was also constant at 0.01 mm$^{-1}$.

Reflected excitation intensity was also recorded in order to monitor variations in the scattering coefficient of the medium. There was no variation in the ratio of fluorescence/scatter when the background absorption coefficient was changed over the range of $\mu_a$=0.0026 to 0.073; however, changes in the scattering coefficient of the medium can alter this ratio. In FIG. 6, the ratio of fluorescence to scattered excitation detected intensities are plotted for a series of solutions, containing the same amount of fluorophore in each (62 $\mu$M of the sulphorhodamine B) but with increasing amounts of Intralipid, to change the scattering coefficient. There is a correlation between the two signals, suggesting that the simultaneous measurement of scattered excitation light in parallel with the fluorescence measurement can be used to normalize the detected fluorescence from the tissue. While the ratio of these two signals is not constant, especially at low scatter coefficients, it may be used to calibrate for differences in fluorescence due to changes in the scattering coefficient of tissue. In this case, the scattering signal is smaller than the excitation simply because only one fiber was used for the scattering detection, while 30 fibers were used for the fluorescence collection (see FIG. 4).

The goal of this study has been to examine the theoretical foundations of micro-sampling of tissue fluorescence for quantitative measurement, and the practical development of a fiber bundle which can accomplish this.

Figure 3:
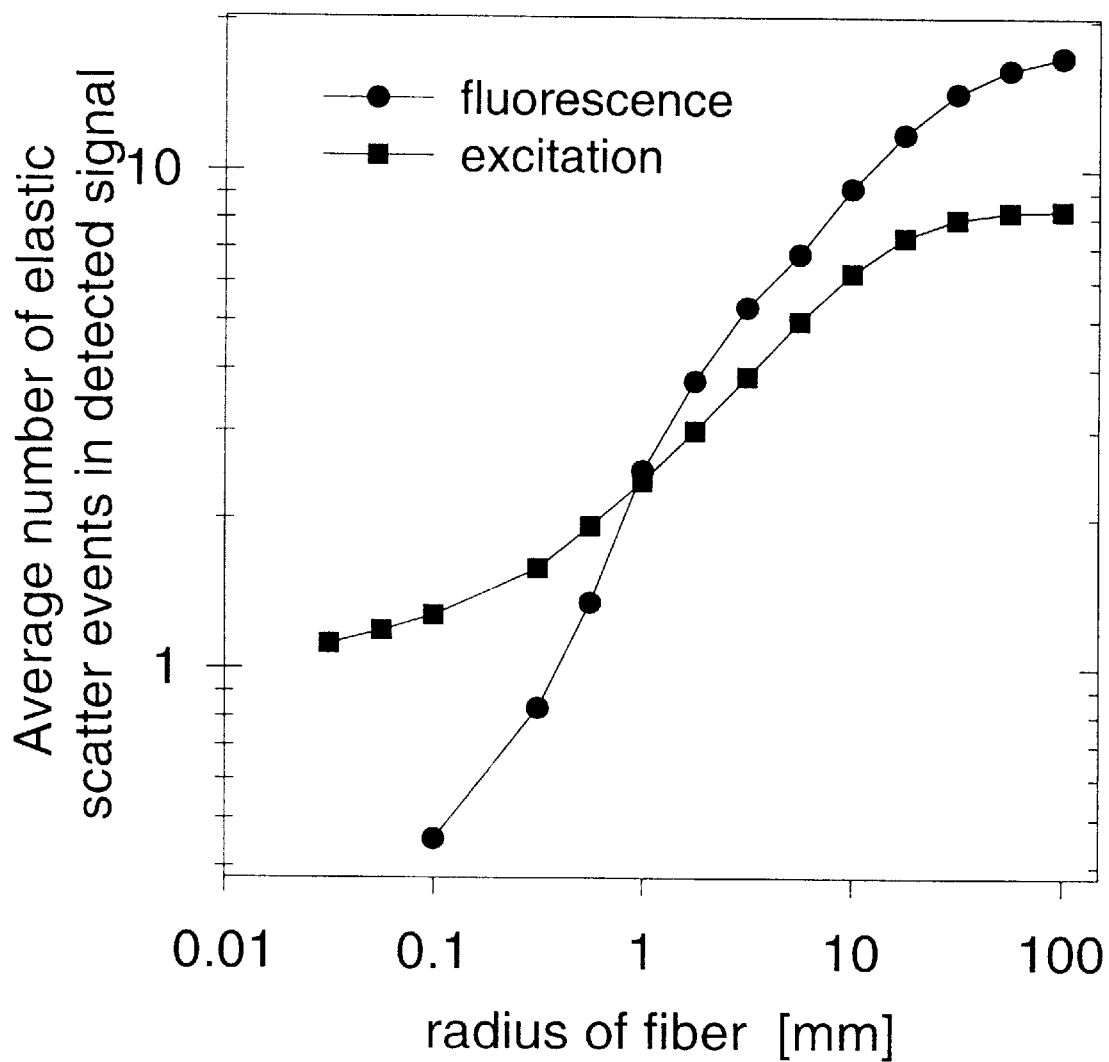
FIG. 3. Theoretical calculations (Monte Carlo) of the average number of scattering events in the detected excitation signal and the detected fluorescence signal versus fiber optic radius. Medium optical properties were as in FIG. 2.

Monte Carlo simulations of the fluorescent light detected from fiber optics give an illustrative prediction, while allowing variation of parameters such as fiber radius, tissue optical properties and fluorophore properties. The simulations used in this study are somewhat idealized, however the results indicate promising results for sampling fluorescence from tissue with small fiber optics. In general, as the size of the fiber decreases to smaller than the mean free path in the tissue (1/ $\mu$s), then the signal is weakly attenuated by the tissue itself. FIG. 3 shows that when a 100 $\mu$m fiber is used that the average number of elastic scattering events in the fluorescent signal is less than 1. This calculation indicates that the average path of the fluorescent signal in tissue is perhaps a distance of 1=100 $\mu$m, which according to Beer's law (I=I$_o$ exp(-$\mu_a$1) ) would have an overall attenuation of 5%, assuming $\mu_a$=0.05 mm$^{-1}$ which is a high value for most tissues. Interestingly, if tissues with higher attenuation are to be used, the fiber diameter could be reduced further to minimize effects of absorption in the tissue. Since fiber optics as small as 10 microns are commercially available, measurement of weakly-scattered fluorescence signals from most tissues should be possible. It should be noted that using small fiber optics to sample the fluorescence in this manner limits the depth sampled in the tissue, so that the applications of this method may be limited ultimately to the surface layers of tissues.

The multi-strand fiber optic probe was developed to increase the intensity of the detected fluorescent light from the tissue. Ideally single fibers could be used, but the detected fluorescence is too low when typical metabolic concentrations of fluorescent dyes are used. The Monte Carlo simulations indicated that for the tissue optical properties used in FIG. 2, that a fiber separation of 0.5 mm would be sufficient to lower the inter-fiber exchange of fluorescent light in the tissue to less than 10%. This estimate is based upon Monte Carlo calculations of the exiting intensity at a distance 500 microns away from the excitation fiber, for $\mu_a$=0.01 and $\mu_s$=1.0. Changes in the tissue optical properties will definitely alter this amount of crosstalk, however it should be noted that these coefficient values are relatively low, and any increase in absorption or scattering will simply decrease the inter-fiber cross talk. In the fiber design here, this distance was taken as a minimum, and the actual distance between fibers was between 0.5 and 1 mm.

Figure 5A:
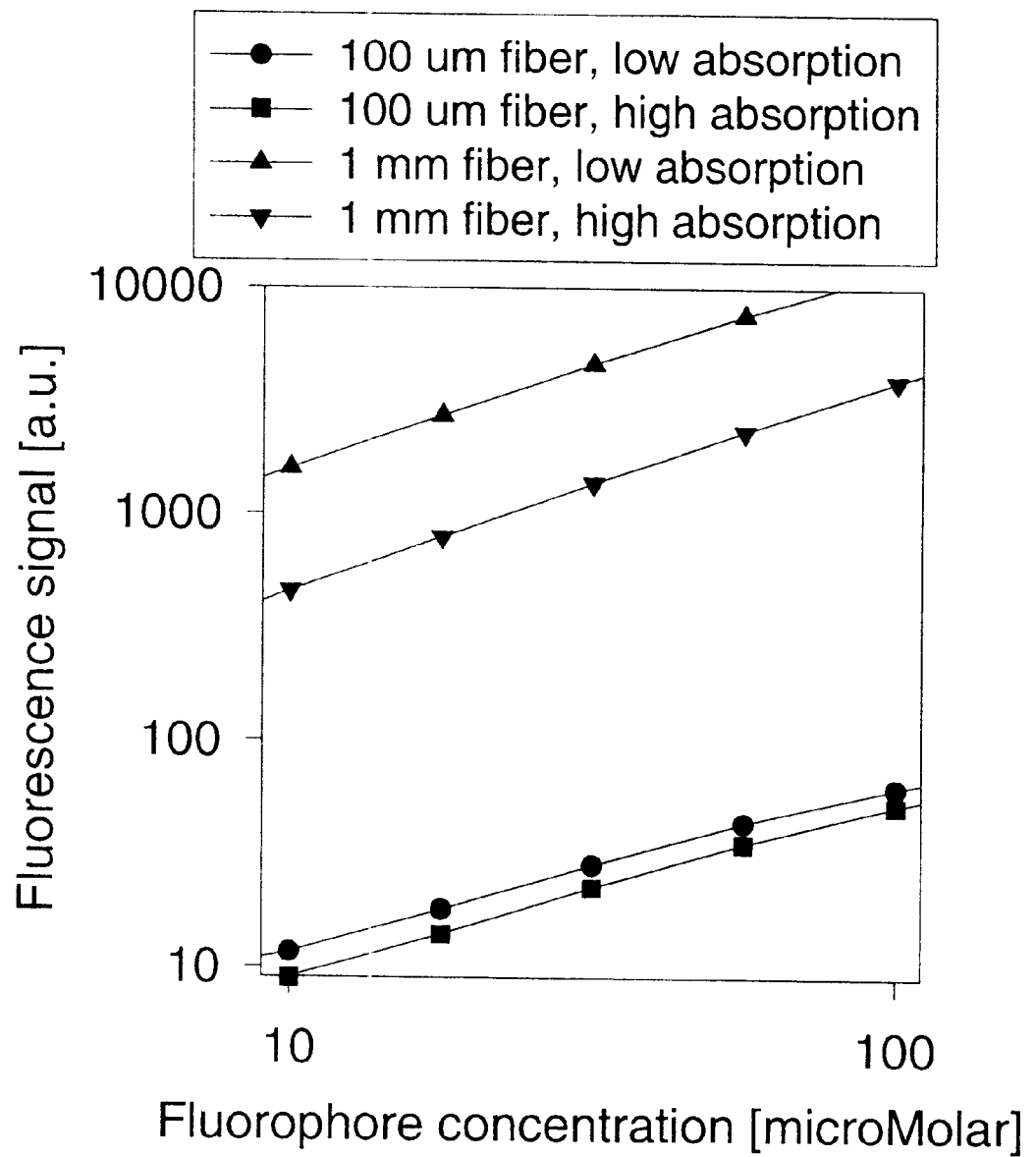
FIG. 5(a). Monte Carlo calculations of fluorescence detected from a fiber optic at the surface of a scattering medium, $\mu_s$=10.0 mm$^{-1}$, g=0.90, using both a 1 mm simulated fiber and a 100 $\mu$m simulated fiber. A range of fluorophore absorption coefficients were used with two different endogenous absorption values of ($\mu_a$=0.003 mm$^{-1}$ and 0.03 mm$^{-1}$.
Figure 5B:
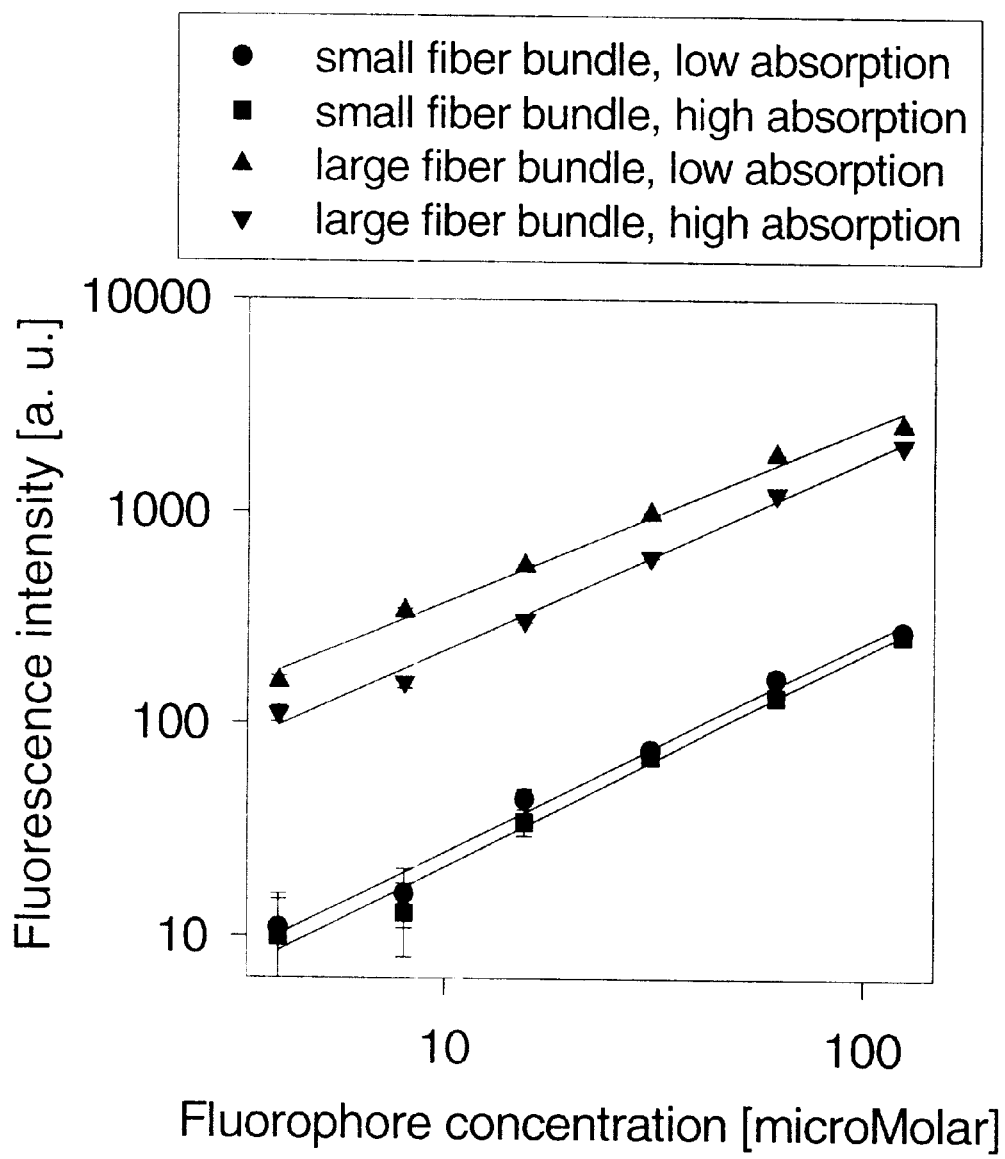
FIG. 5(b). Fluorescence measurements from two similar sets of tissue-simulating solutions containing serial dilutions of fluorophore, with one set containing no absorber ($\mu_a$=0.0026 mm$^{-1}$), and the other containing 1.5% ink ($\mu_a$=0.073 mm$^{-1}$). Measurements were taken both with a standard 1 mm fiber bundle and with the new fiber bundle depicted in FIG. 4 using separated 100 $\mu$m fibers.

The measurements of fluorescence plotted in FIG. 5(b) demonstrate that for solutions with a higher background absorption concentration ($\mu_a$=0.074 mm$^{-1}$) that the detected signal is lower than for solutions with less background absorption ($\mu_a$=0.0026 mm$^{-1}$). In this case, the measurements from the two sets of solutions with the standard fiber bundle (FIG. 5(b) also) differ by 40% on average, whereas the measurements with the specially designed fiber bundle differ by 10% on average. The use of even smaller fiber optics are expected to lower this difference even further. The simulation results plotted in FIG. 5(a) are in good qualitative agreement with the experimental results in (b), as the change in intensity with absorption coefficient of the sample is similar. There are quantitative differences in the experimental and simulated values, but in general the larger fiber demonstrates a sensitivity of the detected intensity to the medium's absorption coefficient, while the small 100 micron fibers minimize this effect.

It should be noted that the scattered excitation signal is sampled from a single 100 micron fiber which is adjacent to one of the excitation fibers, so that the signal has traveled through a thickness of tissue which is larger than the sampled path of the fluorescence signal. This design was used because there is no good method of sampling the scattered light from the same fiber which delivers it, without having significant reflections from both ends of the fiber which will confound the signal.

In summary, it should be noted that the concept of reducing the volume of tissue sampled can lead to quantitatively consistent measurements of fluorescence, independent of the background (or endogenous) absorption present. The system outlined here will be useful to monitor the concentration of photosensitizers taken up in tissues, monitor pharmacokinetics and photobleaching rates in vivo without the need for tissue extraction, or possibly to monitor DNA or protein stains in situ for animal models. The excitation laser to allow excitation of photosensitizers at 440 nm wavelength, improving the optical alignment to allow more light to be captured, and using a series of bifurcated optical fibers to allow easier separation of the scattered excitation light and remitted fluorescence. Previous calculations suggested that this method could be used to detect quantities of fluorophore near 10$^{-7}$ Molar, assuming that an optimized optical system is developed for light collection, and can likely be lower when multiple fibers are used to integrate the signal over larger tissue regions.

The measurement of fluorescence signals from tissue is complicated by photochemical changes in the fluorescence quantum yield, and attenuation of the light by the tissue. While this fiber optic bundle cannot help deduce changes due to the physiochemical environment of the fluorophore, it can help reduce the effect of the light attenuation in the tissue. Thus as applications for fluorescence detection from tissue become more sophisticated, the ability to separate tissue attenuation changes from physio-chemical changes will be more important. This study suggests that detecting fluorescence from regions of tissue which are smaller than the average scattering length of the tissue may be a useful method for quantitative fluorophore measurement, which does not require model interpretation of the light signal.

The Monte Carlo Calculations

Light propagation in tissue can be simulated accurately with a Monte Carlo technique where individual packets of photons are followed as they travel through different scattering and absorption events. One of the main advantages of this type of simulation is the simplicity and versatility of adding specific boundary conditions, source locations and detector positions, especially when these are located in small regions of space. In order to better understand the photophysical interaction of excitation and fluorescent light with tissue using small fiber optics as source-detector probes, a Monte Carlo simulation was developed. This approach was initially used for confocal detection studies, where the light was delivered and detected from the same objective lens. Using fiber optics, the physical simulation is essentially identical, with a small correction to inject and collect photons into the tissue with the numerical aperture of the fiber.

The salient features of our simulation will be outlined. The simulation assumed the photons scattered with an average mean free path governed by the inverse of the scattering coefficient, $\mu_s$, which meant that the average pathlength was given by:

$$l = 1/\mu_s \tag{1}$$

During the simulation the random length of travel before each scattering event is:

$$s_i = \ln(\epsilon_i)/\mu_s \tag{2}$$

where $\epsilon_i$ is a random number between 0 and 1, and $s_i$ is the distance the photon moves for step i. Equation (2) gives a random pathlength which has an average equal to equation (1), i.e. <s>=1. The absorption was added in by attenuating the photon packet according to Beer's law after each scattering event, with an absorption coefficient, $\mu_a$, so that the weight, w, of the photon packet at any time scattering event i, is given by:

$$^sW_i = {}^sW_{i-1} \exp(-{}^s\mu_a s_i) \tag{3}$$

where the script s denotes that it is a scattered excitation wavelength rather than a fluorescent photon wavelength. At the end of the photons packets travel, when the path has crossed a boundary, the weight is added to the total of all the photon packet weights exiting the tissue, to contribute to the calculated light signal, so that the scattered signal, $^S\Phi$, exiting the tissue is:

$$^s\Phi = \sum_{I=1}^{N} {}^sw_i \tag{4}$$

where N is the number of photon packets launched in the simulation. The angle of each scattering event is governed by the phase function, and here the Henyey-Greenstein formula was used since it has been demonstrated to simulate tissue scattering reasonably well. It should be noted that there are other scattering phase functions which are thought to better simulate tissue scatter angles, but the Henyey-Greenstein function is accurate enough for this study, and only requires the input of the average cosine of the scattering angle, g. The absorption event due to the fluorophore was simulated using the probability of Beer's law attenuation, where a comparison was made at each scattering event between a random number $\epsilon$, and the probability of absorption given by:

$$P = \exp(-{}^F\mu_a s) \tag{5}$$

If the random number was less than this probability, than the photon was absorbed by the dye, and generated a fluorescent photon, with a new weight:

$$^F w_i = \phi_{fl}{}^S w_{i-1} \exp(-^F \mu_a s) \quad (6)$$

where the script F refers to fluorescent photon packets, and $\phi_{fl}$ is the fluorescent quantum yield which was kept at 1.0 here for simplicity. A lower fluorescent quantum yield would mean less fluorescent photons were generated and a lower intensity. The fluorescent photons packets were initiated at the site of the absorption event, with an initial isotropic scatter direction. Once a fluorescent photon packet was generated, it was followed in the simulation using the same scattering coefficient, anisotropy parameter, and absorption coefficient, but without any possibility for re-absorption of the fluorescent photons by the dye. The detected fluorescence signal is calculated by summing the weights of all fluorescent photon packets that exit the tissue surface:

$$F_\Phi = \sum_{i=1}^{N} F_{W_i} \quad (7)$$

This simulation is an idealized representation of light scattering, since the scattering and absorption coefficients of the excitation and fluorescence are likely to be different if they are at different wavelengths, however scattering changes in tissue are known to be a modest function of wavelength, and the absorption due to the Ink used in our simulations is not strongly wavelength dependent. The assumption that there was no re-absorption of the fluorescence by the fluorophore is accurate if the Stoke's shift of the molecule is larger than the Q-band absorption peak width and is generally true for the dye used experimentally here.

Figure 1:
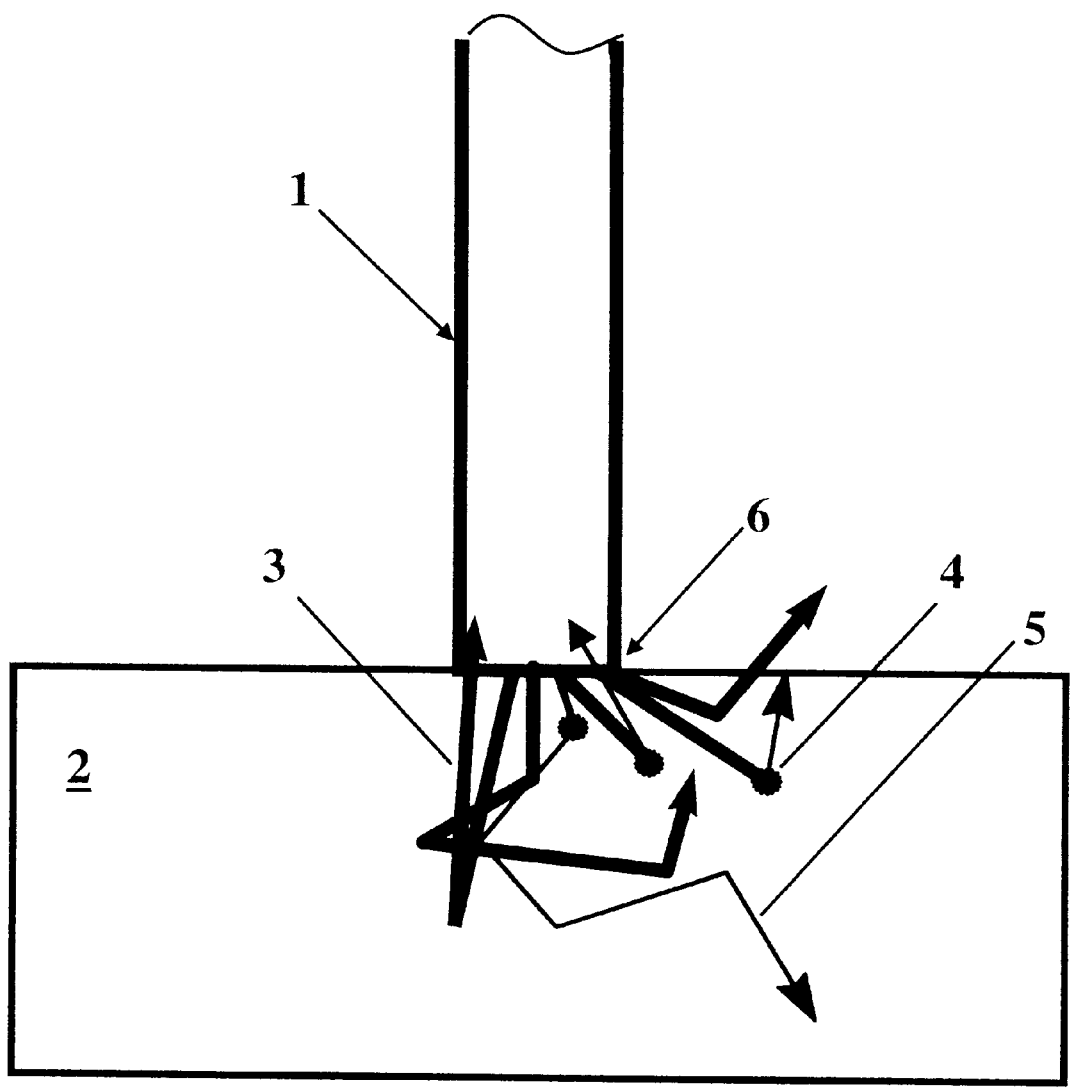
FIG. 1. Schematic diagram of the geometry for both Monte Carlo simulations and experimental measurements of fluorescence from an individual fiber 1 in contact with tissue-simulating media 2. Both excitation (dark arrows, 3) and fluorescence (light arrows, 5) can be captured by the fiber optic 6 when in contact with the medium. Fluorescent events (stars, 4) occur when the photon is absorbed by the fluorophore.
Figure 2A:
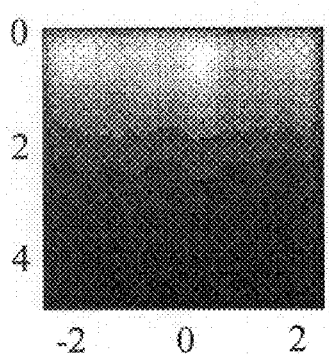
FIGS. 2a-2f. Monte Carlo simulations of excitation fluence in the medium (FIGS. 2a-2c) and fluorescence fluence that is captured by the fiber optic (FIGS. 2d-2f). The left pair of images (FIGS. 2a and 2d) show the excitation and captured fluorescence fluence for a broad beam illumination from the surface. The middle pair of images (FIGS. 2b and 2c) show the same calculations for a 2 mm diameter fiber optic, and the right pair of images (FIGS. 2c and 2f) are for a 100 $\mu$m fiber optic. Scattering media properties were fixed at $\mu_s'$=10.0, $\mu_a$=0.01 mm$^{-1}$, and g=0.90. (Note "$\mu_s'$" is used as the abbreviation for reduced scattering coefficient; "mm$^{-1}$" is used as the abbreviation for units of inverse millimeters; and, "$\mu_a$" is used as the abbreviation for absorption coefficient or absorption concentration.)
Figure 2B:
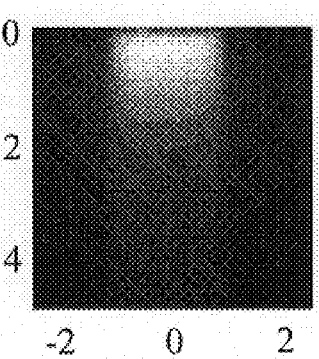
Figure 2C:
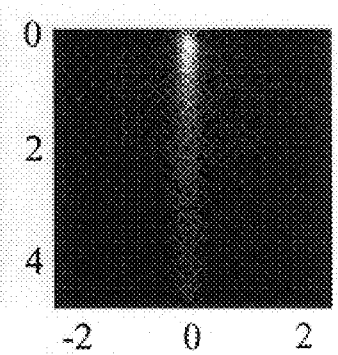
Figure 2D:
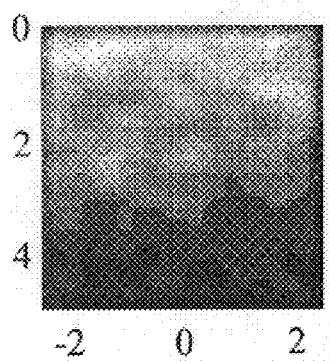
Figure 2E:
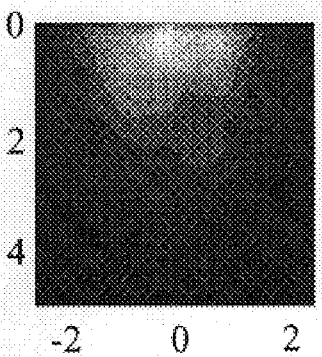
Figure 2F:
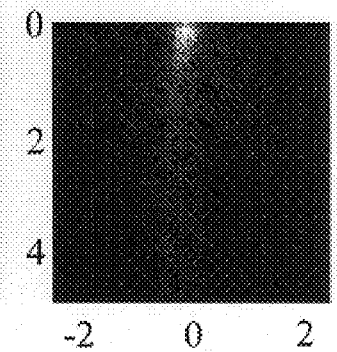

In these simulations a fixed numerical aperture of 0.22 was used with tissue optical properties $\mu_a$=0.01 mm$^{-1}$, $\mu_s$=10.0 mm$^{-1}$ and g=0.90. The geometry of the simulation is shown in FIG. 1, where the fiber is in orthogonal contact with the tissue surface and excitation photons and fluorescence photons are illustrated as scattering in the medium. Simulations were completed for various fiber diameters and fluorophore concentrations in order to examine the average number of scattering events in the detected signal, as well as to visualize the fluence or photon density, which is defined as the number of photons passing through a unit spherical area within the medium.

SUMMARY

The essence of the invention in its preferred embodiment is that a fiber optic bundle is designed to contain 30 individual fibers that have a diameter of 100 microns wherein each fiber contained in the bundle is separated from the other fibers by approximately 500 microns at the end of the bundle that comes in contact with the surface of the tissue; there is no separation of the bundle on the opposite end. Preferably, the fibers are arranged such that the tissue contact end of the bundle is generally circular in cross-section. Although the preferred embodiment employs the separation by said 500 microns, the essence of the invention is to separate the fibers whether performing the evaluation of tissue or other type of application in order to obtain improved readings of light from tissue. For example, the separation of the fibers could be as little as 300 microns or as much as 2,000 microns or 2 millimeters, but is preferably no more than 1,000 microns or 1 millimeter (1,000 microns equals one millimeter; a millimeter is equal to one thousandth of a meter) from each other on the tissue contact surface. In addition, the number of fibers in a fiber optic bundle does not have to be exactly 30 individual fibers; the number of fibers in a fiber optic bundle can vary, for example from 2 to 500 fibers, but more preferably between 10 and 100 fibers. Moreover, the diameter of each individual fiber is preferably at least 10 microns, and can be up to 500 microns, but preferably no more than 200 microns; the purpose of limiting the diameter of each fiber is that the fiber should be thin enough to minimize the multiple scattering in the captured luminescent signal. The improvement is that a bundle of fiber optics are separated by a designed distance at the tissue surface in order to enable improved readings for the evaluation and diagnosis of the tissue.

In the preferred embodiment, a fluorescent or phosphorescent chemical or drug is introduced into a patient and said bundle of optic fibers are placed in contact with the tissue to be examined. Thereafter, light which is capable of being absorbed by said fluorescent or phosphorescent chemical or drug is injected into said fiber bundle and then the fluorescent or phosphorescent light generated by the chemical or drug is captured back into the fiber bundle. Said light that is captured back into the fiber bundle is separated by a dichroic mirror and then delivered into a detector capable of transmitting the optical intensity into an electrical signal. Said electrical signal will provide a basis for determining the concentration of said chemical or drug present in the tissue. In addition, some of the light that is captured back into the fiber bundle is analyzed by a second detector and a correction for different tissues scattering is completed by application of a calibration of the captured luminescent light to the captured scattered excitation light. The second detector could be combined and or eliminated depending on the capabilities of the first detector.

We claim:

1. A method for detecting fluorescence or phosphorescence signals from a tissue sample containing a fluorophore or phosphor concentration therein, the method comprising the steps of:

providing an optic probe for detecting luminescence from a tissue sample containing a fluorophore or phosphor concentration therein, the optic probe having a plurality of optic fibers maintained in a bundle, each of the plurality of optic fibers having, a first end where the fibers are arranged in a substantially contiguous array and collectively form a first bundle end, and a tissue contact end where the fibers are arranged in a spaced apart arrangement at a substantially constant minimal spacing between near neighbor fibers, the spaced apart arrangement forming a tissue contact bundle end for placement against the tissue sample;

aligning the first bundle end with an optical detection device;

placing the tissue contact bundle end with a site on the tissue sample;

passing an excitation light through the optic fibers; and, monitoring fluorescence or phosphorescence transmitted through the optic fibers from the tissue sample with the optical detection device.

2. A method for detecting fluorescence or phosphorescence signals from a tissue sample containing a fluorophore or phosphor concentration therein, the method comprising the steps of:

providing a plurality of optic probes, each optic probe having a plurality of optic fibers maintained in a bundle, each of the plurality of optic fibers having, a first end where the fibers are arranged in a substantially contiguous array and collectively form a first bundle end, and a tissue contact end where the fibers are arranged in a spaced apart arrangement at a substantially constant minimal spacing between near neighbor fibers, the spaced apart arrangement forming a tissue contact bundle end for placement against the tissue sample;

aligning the first bundle end of each of the plurality of optic probes to an optical detection device;

placing the tissue contact bundle end of each of the plurality of optic probes with the tissue sample;

passing an excitation light through the optic fibers;

monitoring fluorescence or phosphorescence signals transmitted through the fibers of each of the optic probes from the tissue sample with the optical detection device; and, integrating said fluorescence or phosphorescence signals.

3. An optic probe for detecting luminescence from a tissue sample containing a fluorophore or phosphor concentration therein, the optic probe comprising:

a plurality of optical fibers maintained in a bundle, each of said plurality of optic fibers having,
  a first end where said fibers are arranged in a substantially contiguous array and collectively form a first bundle end, and
  a tissue contact end where said fibers are arranged in a spaced apart arrangement at a substantially constant minimal spacing between near neighbor fibers, said spaced apart arrangement forming a tissue contact bundle end for placement against the tissue sample.

4. The optic probe of claim 3 wherein said bundle of a plurality of optic fibers is generally arranged circular in cross-section.

5. The optic probe of claim 3 wherein said plurality of optic fibers ranges from 2 optic fibers to 500 optic fibers.

6. The optic probe of claim 5 wherein said plurality of optic fibers ranges from 10 optic fibers to 100 optic fibers.

7. The optic probe of claim 6 wherein said plurality of optic fibers is about 30 optic fibers.

8. The optic probe of claim 3 wherein said optic fibers have diameters ranging from 10 microns to 500 microns.

9. The optic probe of claim 8 wherein said diameters range from 10 microns to 200 microns.

10. The optic probe of claim 9 wherein said diameters are about 100 microns.

11. The optic probe of claim 3 wherein one of said plurality of optical fibers is separated from said bundle at said first end.

12. The optic probe of claim 3 wherein said substantially constant minimal spacing separating said near neighbor fibers at said tissue contact bundle end of said bundle ranges from 300 microns to 2,000 microns (2 mm).

13. The optic probe of claim 12 wherein said substantially constant minimal spacing separating said near neighbor fibers at said tissue contact bundle end of said bundle is about 1,000 microns (1 mm).

* * * * *